United States Patent [19]
Franetzki

[11] Patent Number: 4,759,371
[45] Date of Patent: Jul. 26, 1988

[54] IMPLANTABLE, CALIBRATEABLE MEASURING INSTRUMENT FOR A BODY SUBSTANCE AND A CALIBRATING METHOD

[75] Inventor: Manfred Franetzki, Uttenreuth, Fed. Rep. of Germany

[73] Assignee: Siemens Aktiengesellshaft, Berlin & Munich, Fed. Rep. of Germany

[21] Appl. No.: 44,608

[22] Filed: May 1, 1987

[30] Foreign Application Priority Data

May 2, 1986 [DE] Fed. Rep. of Germany ....... 3614821

[51] Int. Cl.$^4$ ............................................. A61B 5/00
[52] U.S. Cl. ..................................... 128/653; 128/632
[58] Field of Search ............... 128/632, 633, 634, 635, 128/637, 639; 604/31, 190, 240; 204/403, 415

[56] References Cited
U.S. PATENT DOCUMENTS 4,543,955 10/1985 Schroeppel ........................ 128/635
4,633,878 1/1987 Bonbardieri ...................... 128/635
4,650,547 3/1987 Gough ................................ 128/635
4,680,268 7/1987 Charh ............................ 128/635 X Primary Examiner—Edward M. Coven
Attorney, Agent, or Firm—Hill, Van Santen, Steadman & Simpson

[57] ABSTRACT

An implantable measuring instrument for a body substance for use in controlling an implantable infusion device has a housing with a recess covered by a semipermeable membrane which permits transfer of molecules of a selected size therethrough. The volume defined by the recess and the membrane is in communication with an expandable chamber in the housing and a channel leading directly or indirectly via an additional membrane to a sensor for the body substances to interest. The channel is also in communication with a pump. There is also provided another recess covered by a pierceable, resealable septum. A conduit leads from the septum to the sensor. For calibrating the instrument, a cannula is introduced through the septum, and all of the fluid in the conduit leading to the sensor is withdrawn by suction. A known calibrating substance is then introduced by the cannula through the septum until the conduit leading to the sensor is filled. Data can then be acquired from the sensor, and if necessary one or more operating parameters of the instrument can be re-set. This procedure can also be used for rinsing and/or reactivating the sensor.

18 Claims, 2 Drawing Sheets

IMPLANTABLE, CALIBRATEABLE MEASURING INSTRUMENT FOR A BODY SUBSTANCE AND A CALIBRATING METHOD

BACKGROUND OF THE INVENTION

1. Field of the Invention

The present invention relates to an implantable, calibrateable measuring instrument for a body substance and a calibrating method therefor, and in particular to such an instrument which can be used for controlling an implantable infusion device, for example an insulin infusion device.

2. Description of the Prior Art

Instruments are known for measuring a body substance which can be implanted together with an infusion device for controlling the medication dose to the patient. It is also known to equip such instruments with a calibration means so that periodic adjustment of the instrument can be made, if necessary.

Ideally, control of an implanted medication dosing device is made with a co-implanted measuring instrument which monitors the body parameter to be controlled via a measuring sensor. A control signal for the metering pump in the infusion device is derived from the electronically processed measured signal. An example of such a device is known from diabetes therapy. In such devices, the measured variable and the controlled parameter are the glucose concentration in the body, for example, in the blood, the connecting tissue, or the peritoneum of the patient. The controlled variable is the insulin conveying rate. In such a device, known as a closed-loop device, the measuring sensor is usually subject to drift. Such drift can be associated with the zero point, the slope of the processed signal, or the shape of the processed signal, thus requiring periodic calibration.

SUMMARY OF THE INVENTION

It is an object of the present invention to provide an implantable calibrateable measuring instrument for a body substance having a calibration means therein which permits existing drift in the measured signal of the sensor to be monitored and compensated.

It is another object of the invention to provide a measuring instrument for an implantable infusion device which may be implanted in the body of a patient over a long period of time.

It is a further object of the present invention to provide a method for use in calibrating such an instrument.

The above object is achieved in accordance with the principles of the present invention in an implantable instrument having a housing with a recess therein covered by a semi-permeable membrane which permits molecules of the size of interest to pass therethrough. The space formed between the recess and the membrane is in communication with an expandable storage chamber and a channel leading directly or indirectly to a measuring sensor. The channel is also in communication with a conveying means, such as a pump. A conduit is provided between the sensor and another recess in the housing, which recess is covered by a pierceable, releasable septum. By means of the membrane, either a filtrate or a dialysate may be obtained. In normal operation, the substance to be measured passes through the membrane and is sensed by the sensor. In the case of a filtrate, it is discharged via the pump back into the body of the patient. In one embodiment, where an ultra-filtrate accumulates at the inner side of the membrane, the filtrate is returned by the pump via a discharge path opening directly to the patient. In the case of dialysis, where a dialysate is obtained, an embodiment may be chosen in which the discharge path from the pump is through the expandable chamber and returns to the space between the recess and the membrane, wherein an equilibrum is maintained on both sides of the membrane.

Calibration of the instrument is undertaken by introducing a cannula, such as the needle of a syringe, through the septum and withdrawing the fluid in the housing by suction, for example until the expandable chamber collapses. A calibration substance is then introduced into the conduit leading from the septum to the sensor via the same or a different cannula, and the operation of the sensor can be monitored by known methods, such as telemetry using a transmitting coil. The sensor can then be re-set, if necessary, again by known methods such as telemetry. Such data acquisition and re-setting can be accomplished as is known, for example, from heart pacemaker technology.

DESCRIPTION OF THE PREFERRED EMBODIMENTS

Figure 1:
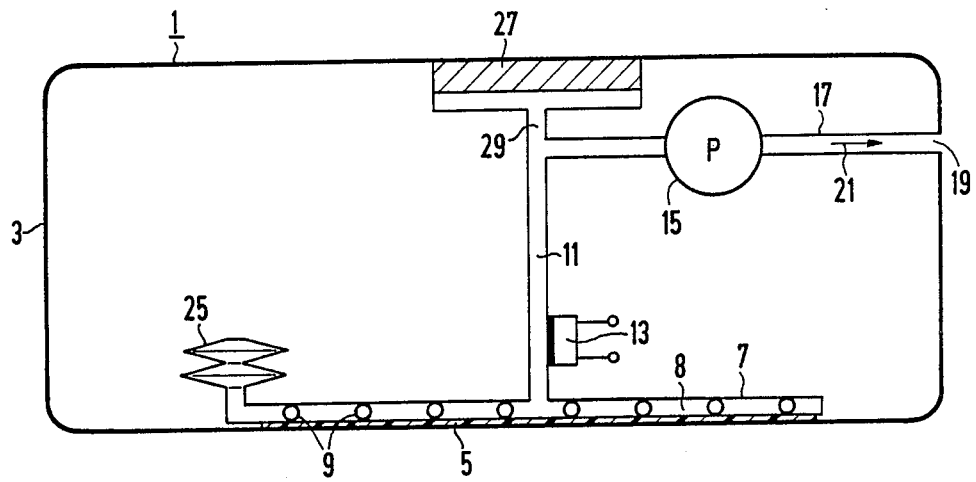
FIG. 1 is a sectional view of a measuring instrument for an ultra-filtrate constructed in accordance with the principles of the present invention.

For like elements the same reference numerals are used in FIGS. 1-4.

A measuring instrument implantable into the body of a patient and constructed in accordance with the principles of the present invention is generally referenced at 1 in FIG. 1. The measuring instrument 1 is designed for measuring or analyzing a body fluid, in particular glucose content in a body liquid. The instrument 1 has a housing 3 which is relatively flat. A recess in one surface of the housing 3, for example an end face thereof, is provided with a large-area semi-permeable membrane 5. The membrane 5 may have an area of, for example, about 20 cm$^2$. Behind the membrane 5 is a flat pot-shaped capsule 7 in the housing 3. A supporting grid 9 for the membrane 5 may be disposed in the space 8 between the membrane 5 and the capsule 7. The space 8 formed within the recess covered by the membrane 5 is in fluid communication with a channel 11 in the interior of the housing 3. A measuring sensor 13 is disposed within or along the channel 11. The channel 11 is also in fluid communication with a conveying means 15, such as an electrical pump P. The output side of the conveying means 15 is in communication with an output path or discharge channel, which in the embodiment of FIG. 1 is a conduit 17 leading directly to a discharge opening 19 in the housing 3 through which opening 19 the fluid is returned to the body. Electronic means (not shown) for signal processing are connected to the sensor 13.

The space 8 between the membrane 5 and the capsule 7 is also in fluid communication with an expandable storage chamber 25, such as a bellows. The storage chamber 25 has elastic walls which normally cause the chamber 25 to collapse or to compress. Instead of chamber 25, another element of a given elasticity may be used in the fluid path, such as the membrane 5 or the capsule 7, for forming an expandable chamber.

The channel 11 is also in fluid communication with a further channel 29 leading to another recess in the housing 3, which is covered by a pierceable, resealable septum 27. Thus, a fluid flowpath consisting of the channels 29 and 11 and the volume 8 between the recess 7 and the membrane 5 is provided between the expandable chamber 25, the sensor 13 and the inner side of the septum 27.

In the embodiment of FIG. 1, by operation of the conveying means 15, an ultra-filtrate arising at the inner side of the membrane 5 is transported therefrom back into the body of the patient along or through the measuring sensor 13 and through the discharge opening 19.

The membrane 5 is dimensioned such that only certain substances from the fluid body substance at the exterior of the housing 3, namely those having a molecule size smaller than a prescribed molecule size, can pass therethrough as said filtrate. For example, the membrane 5 may be dimensioned to be transmissive for molecules up to the size of glucose molecules.

For starting calibration of the measuring sensor 13, a cannula, such as the needle of a syringe (not shown) is introduced through the septum 27. The liquid contained in the aforementioned flowpath is withdrawn by suction until the storage chamber 25 has collapsed. The syringe is then emptied outside of the patient. The same or a different syringe filled with a calibrating substance is then introduced through the septum 27. The calibrating substance is emptied into the flowpath. The calibrating substance is injected until the space up to the measuring sensor 13 is completely filled, thereby insuring that the calibrating substance is present at the location of the measuring sensor 13. In accord with the measured value supplied by the measuring sensor 13, the sensor 13 and the aforementioned electronic means are re-set (re-balanced), if necessary, or left as is. Such re-setting is undertaken from outside the instrument 1 by data communication techniques known with respect to implantable devices in general, such as, for example, signal transmission by the use of antennae such as coils (telemetry). In this manner, re-calibration of the implanted measuring sensor 13 is possible from the exterior of the patient without surgery.

During re-calibration, for example, the gain (sensitivity) or the zero level of the afore-mentioned electronic means may be re-adjusted such, that a predetermined (known) concentration of the calibrating substance again corresponds to a certain output signal. Alternatively, re-calibration may be such that a modified correspondence between concentration and output signal is determined, recorded for example in a look-up table and/or displayed. This takes place in a communication device outside the patient.

Figure 2:
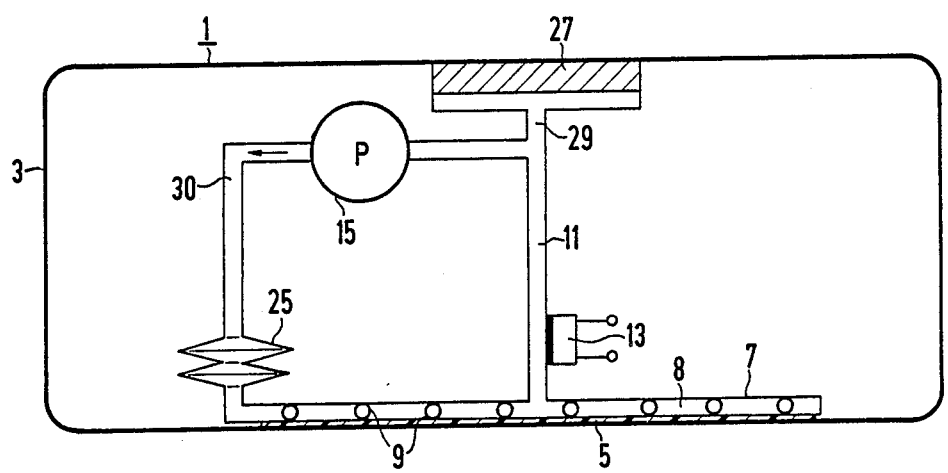
FIG. 2 is a sectional view of a measuring instrument for a dialysate constructed in accordance with the principles of the present invention.

Another embodiment of the measuring instrument 1 is shown in FIG. 2. In this embodiment a dialysate is supplied to the measuring sensor 13 instead of an ultrafiltrate. Components in the embodiment of FIG. 2 identical to those in the embodiment of FIG. 1 are provided with the same reference symbols. In the embodiment of FIG. 2, the discharge path from the output of the conveying means 15 does not lead fluid back to the patient via a discharge opening 19, as in the embodiment of FIG. 1. Instead, the output of the conveying means 15 is in fluid communication with the storage chamber 25 via a channel 30. A closed circulation flowpath thus arises, consisting of the conveying means 15, the line 30, the storage chamber 25, the space 8 between the membrane 5 and the capsule 7, and the channel 11 in which the measuring sensor 13 is disposed.

In contrast to the embodiment of FIG. 1, no noticeable suction of body fluid in the direction of the membrane 5 takes place under the effect of conveying means 15.

In the second circulation path—along with the dialysate—an enzyme (introduced at the beginning of a measuring period) may be pumped cyclically. Thus, the enzyme does not have to be bound to or absorbed by the sensor 13, which, nevertheless, may be an enzyme sensor.

In the embodiment of FIG. 2, the membrane 5 is selected such that a concentration equilibrium in the fluid in the body tissue at the exterior of the housing 3 and the substance in the volume 8 between the inner side of the membrane 5 and the capsule 7 is maintained. Such a technique is known from dialysis technology. The concentrations of the respective substances in the flowpath 11 of the measuring instrument 1 which are transmitted through the membrane 5 balance those in the body tissue at the exterior of the membrane 5. The signal from the sensor 13 thus corresponds to the current concentration of the measured substance in the body. This concentration signal is only delayed by the conveying time required for transportation from the membrane 5 to the sensor 13.

Calibration of the embodiment of the instrument shown in FIG. 2 is done as described above in connection with the embodiment of FIG. 1. Through a cannula, for example of a syringe, fluid is first withdrawn by suction from the flowpath until the storage chamber 25 is completely empty and has collapsed. Subsequently, a calibrating substance is introduced into the flowpath via the same cannula left in the patient. The arrangement of the storage chamber 25 following the sensor 13 insures that the calibrating substance is present at the location of the measuring sensor 13. If necessary, the measuring sensor 13 is re-set in the same manner described above, for example by telemetry.

If the measuring sensor 13 requires a substance for making the desired analysis, which substance is consumed or which loses its activity over time, the de-activated substance can be removed from the flowpath 29, 11, 25 through the septum 27 and replaced by a fresh substance. This substance again may be an enzyme which is necessary for the sensor 13 to carry out its intended function. Additionally, rinsing procedures can be undertaken in a similar manner to remove deposits on the measuring sensor 13, or in the flowpath 29, 11, or in the storage device 25. A re-activation of the measuring sensor 13 is also possible dependent on the substance used in the rinsing process. This may be important, if the sensor 13 has become "poisoned", i.e. ineffective, for example, due to a substance generated during measurement or analysis.

Figure 3:
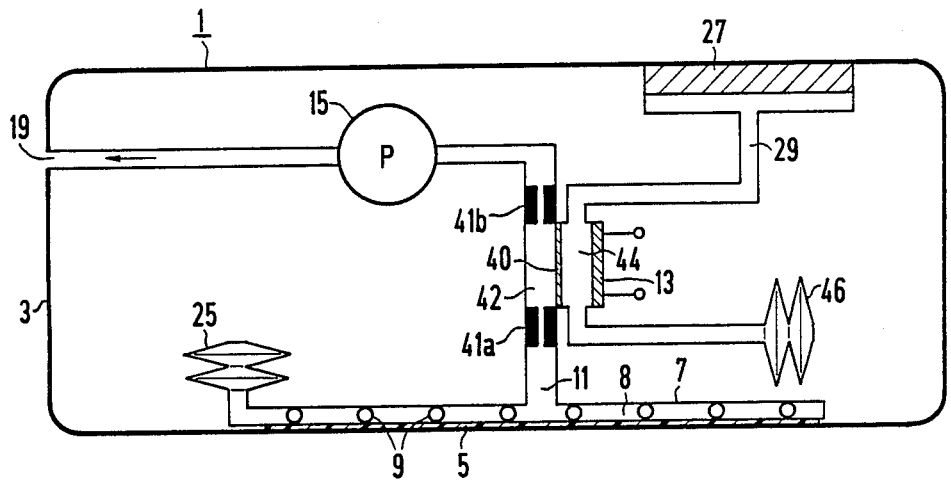
FIG. 3 is a sectional view of a measuring instrument similar to FIG. 1, but having a first and a second measuring chamber and an enzyme sensor, in accordance with the principles of the present invention.
Figure 4:
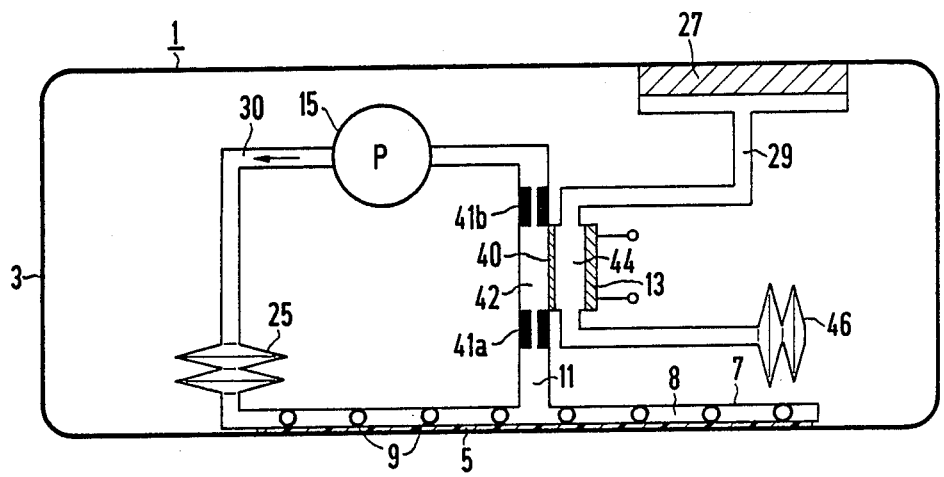
FIG. 4 is a sectional view of a measuring instrument similar to FIG. 2, but having a first and a second measuring chamber and an enzyme sensor, in accordance with the principles of the present invention.

In FIGS. 3 and 4 two additional embodiments of an implantable measuring instrument 1 are shown. In these embodiments, the measuring sensor 13 may be, in particular, an enzyme sensor. The embodiment of FIG. 3 distinguishes itsef from the embodiment of FIG. 1 in which an additional semi-permeable membrane 40 is arranged in the channel 11 instead of the measuring sensor 13. In addition, there is provided a flow-restricting location 41a, 41b in the channel 11 in front of and behind the membrane 40, respectively. By means of the additional membrane 40, a first chamber 42 and a second chamber 44 are formed. The first chamber 42 has the restricting locations 41a and 41b, respectively, at its inlet and outlet. The conveying means 15 is connected to the outlet. The second chamber 44 is separated or divided from the first chamber 42 by means of the additional memebrane 40. At the other side of this membrane 40, the measuring sensor 13 is disposed in the second chamber 44. As specified above, the sensor 13 preferably is an enzyme sensor. In this embodiment the second chamber 44 is in fluid communication with the space behind the septum 27 via the conduit or flowpath 29. There is also provided an additional buffer chamber or storage element 46 which is in fluid communication with the second chamber 44. The measuring sensor 13 is an enzyme sensor which contains a fixed or bound enzyme. Alternately, another type of enzyme sensor may be used, provided that the communication conduit 29, 44, and 46 is filled with a liquid enzyme.

In the embodiment according to FIG. 3, the ultra-filtrate obtained by the membrane 5 along with the body substance to be measured is conveyed to the first chamber 42 when the conveying means 15 is in operation. By means of a concentration balancing procedure, the body substance to be measured is transferred from the first chamber 42 via the semi-permeable membrane 40 into the second chamber 44. As a consequence, the measuring sensor 13 funishes a signal, which corresponds to the concentration of the body substance to be measured.

The embodiment according to FIG. 3 is characterized by the fact that not the entire conduit system that contains the ultra-filtrate has to be rinsed by a substance transferred from outside and that the measuring sensor 13 has to be calibrated therewith; instead only the second chamber 44, located immediately in front of the measuring sensor 13, is accessable via the septum 27 and may be rinsed, as described above. In case that an enzyme sensor working with a liquid enzyme is used, the enzyme may be replaced during this procedure. Alternately, a fixed or bound enzyme may be re-activated.

In systems that consume the measuring substance, in particular in systems having an enzyme sensor or an electrocatalytic sensor, there is the additional possibility of re-calibrating the zero-level. In sensors of this type, for example, glucose is transferred into glucone acid.

For the purpose of zero-level calibration of the measuring sensor 13, the conveying means 15 is switched off for a period of time until the measuring substance is completely consumed. The signal which is now obtained from the measuring sensor 13 corresponds to the zero-point signal and may be used for the re-adjustment or re-calibration of the zero-point of the system. The constricting locations 41a, 41b allow only a very small diffusion into the first chamber 42.

An advantage of this embodiment resides in the reduction of the consumption of enzyme, since a reaction, that is the consumption of enzyme, takes place only immediately after filling of the first chamber 42; such reaction ceases between the measurements of the system.

The calibration procedure of the measuring sensor 13 corresponds to the procedure described in conjunction with FIG. 1.

The embodiment according to FIG. 4 is similar to the embodiment shown in FIG. 1. In comparison to FIG. 3, a dialysate is obtained by means of the membrane 5, instead of an ultra-filtrate. The circulation of the dialysate corresponds to the circulation described in conjunction with FIG. 2. The arrangement of the measuring sensor 13 and an additional membrane 40 corresponds to the embodiment shown in FIG. 3. In other words, again an additional membrane 40 is used for forming a first and a second chamber 42 and 44, respectively. In this embodiment, the calibration is performed corresponding to the procedure described with reference to FIG. 1. Also, a zero-point re-adjustment of the measuring sensor 13 may be carried out, as described in conjunction with FIG. 3.

With the embodiment shown in FIGS. 3 and 4, such enzyme sensor systems may be used in which the enzyme is provided as a liquid substance in a conduit system comprising the second chamber 44 and the sensor 13. The membrane 40 in FIG. 3 and the membranes 5 and 40 in FIG. 4 prevent the enzyme from leaving the measuring instrument 1 and entering into the body of the patient, where such an enzyme may have a toxic effect. In the embodiment according to FIG. 4, a double protection is provided, due to the provision of the two membranes 5 and 40.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable measuring instrument for a body substance, comprising:
    an implantable housing having a first recess therein covered by a semi-permeable membrane which admits a selected body substance therethrough;
    a channel in fluid communication with the volume between said recess and said membrane;
    measuring means communicating with said channel for measuring said selected body substance;
    a conveying means for circulating fluid containing said body substance along said measuring means and having an output connected to an output path;
    an expandable storage means in fluid communication with said volume between said membrane and said recess;
    a second recess in said housing in fluid communication with said measuring means; and
    a pierceable, resealable septum covering said second recess adapted for the introduction and withdrawal of a cannula therethrough.

2. The measuring instrument as claimed in claim 1, wherein said measuring means comprises a measuring sensor for monitoring an ultra-filtrate, and wherein said semi-permeable membrane has a permeation characteristic selected for permitting said ultra-filtrate to accumulate on a side of said membrane facing said first recess by operation of said conveying means.

3. The measuring instrument as claimed in claim 2 wherein said membrane has a permeation characteristic selected for admitting molecules therethrough up to the size of a glucose molecule.

4. The measuring instrument as claimed in claim 1, wherein said output path is a discharge channel leading directly from said output of said conveying means to an exterior of said housing.

5. The measuring instrument as claimed in claim 1, further comprising a further channel connecting said output of said conveying means to said storage means, and wherein said output path is a path through said further channel, said storage means, said volume between said recess and said membrane, and said channel.

6. The measuring instrument as claimed in claim 5, wherein said semi-permeable membrane has a permeation characteristic selected for maintaining an equilibrium concentration of at least one body substance on both sides thereof.

7. The measuring instrument as claimed in claim 1, wherein said measuring means comprises a measuring sensor disposed in said channel.

8. The measuring instrument as claimed in claim 1, wherein said measuring means comprises an additional semi-permeable membrane separating a first chamber from a second chamber, wherein said measuring means comprises a measuring sensor disposed in said second chamber, wherein said first chamber communicates with said channel, and wherein said septum communicates with said second chamber.

9. An implantable measuring instrument for a body substance, comprising:
- a housing having a first recess therein;
- a semi-permeable membrane covering said recess and defining a volume between said membrane and said recess, said membrane having a permeation characteristic for transmitting molecule of a size corresponding to said body substance;
- an expandable storage means in said housing in fluid communication with said volume;
- a channel in said housing in fluid communication with said volume;
- a sensor for measuring said body substance disposed in said channel;
- a pump having an input in fluid communication with said channel and having an output;
- a discharge channel connected to said output of said pump and leading to an exterior of said housing;
- a second recess in said housing in fluid communication with said channel; and
- a pierceable, resealable septum covering said second recess adapted for permitting the introduction and withdrawal of a cannula therethrough, said cannula, when introduced through said septum, being in fluid communication with said channel, said sensor, said volume and said storage chamber.

10. An implantable measuring instrument for a body substance, comprising:
- a housing having a first recess therein;
- a semi-permeable membrane covering said first recess and defining a volume between said membrane and said recess, said membrane having a permeation characteristic selected for maintaining an equilibrum concentration of said body substance on both sides thereof;
- an expandable storage means in fluid communication with said volume;
- a channel in said housing in fluid communication with said volume;
- a sensor for measuring said body substance disposed in said channel;
- a pump having an input in fluid communication with said channel and having an output in fluid communication with said storage means, whereby an output path for fluid from said pump is formed leading through said storage means, through said volume, and through said channel;
- a second recess in said housing in fluid communication with said channel; and
- a pierceable, resealable septum covering said second recess adapted for permitting the introduction and withdrawal of a cannula therethrough, said cannula, when introduced through said septum, being in fluid communication with said channel, said measuring sensor, said volume, and said storage chamber.

11. An implantable measuring instrument for a body substance, comprising:
- a housing having a first recess therein;
- a semi-permeable membrane covering said recess and defining a volume between said membrane and said recess, said membrane having a permeation characteristic selected for transmitting molecules of a size corresponding to said body substance;
- an expandable storage means in said housing in fluid communication with said volume;
- a channel in said housing in fluid communication with said volume;
- an additional semipermeable membrane dividing a first chamber from a second chamber, said first chamber communicating with said channel;
- a sensor for measuring said body substance disposed in said second chamber;
- a pump having an input in fluid communication with said channel and having an output;
- a discharge channel connected to said output of said pump and leading to an exterior of said housing;
- a second recess in said housing in fluid communication with said second chamber; and
- a piercable, resealable septum covering said second recess adapted for permitting the introduction and withdrawal of a cannula therethrough, said cannula, when introduced through said septum, being in fluid communication with said second chamber and said sensor.

12. The measuring instrument as claimed in claim 11, wherein an additional expandable storage means communicates with said second chamber.

13. The measuring instrument as claimed in claim 11, wherein said first chamber has an inlet and an outlet for passing said body substance therethrough, and wherein flow restricting means are associated with said inlet and said outlet.

14. The measuring instrument as claimed in claim 11, wherein said second chamber contains, inter alia, an enzyme.

15. An implantable measuring instrument for a body substance, comprising:
- a housing having a first recess therein;
- a semi-permeable membrane covering said first recess and defining a volume between said membrane and said recess, said membrane having a permeation characteristic selected for maintaining an equilibrum concentration of said body substance on both sides thereof;
- an expandable storage means in fluid communication with said volume;
- a channel in said housing in fluid communication with said volume;
- an additional semipermeable membrane dividing a first chamber from a second chamber, said first chamber communicating with said channel;

a sensor for measuring said body substance disposed in said second chamber;

a pump having an input in fluid communication with said channel and having an output in fluid communication with said storage means, whereby an output path for fluid from said pump is formed leading through said storage means, through said volume, and through said channel;

a second recess in said housing in fluid communication with said second chamber; and a pierceable, resealable septum covering said second recess adapted for permitting the introduction and withdrawal of a cannula therethrough, said cannula, when introduced through said septaum, being in fluid communication with said second chamber and said measuring sensor.

16. The measuring instrument as claimed in claim 15, wherein an additional expandable storage means communicates with said second chamber.

17. The measuring instrument as claimed in claim 15, wherein said first chamber has an inlet and an outlet for passing said body substance therethrough, and wherein flow restricting means are associated with said inlet and said outlet.

18. The measuring instrument as claimed in claim 15, wherein said second chamber contains, inter alia, an enzyme.

* * * * *